United States Patent [19]

Johnson

[11] Patent Number: 5,622,622
[45] Date of Patent: Apr. 22, 1997

[54] ULTRAVIOLET STERILIZER AND SOURCE OF IONIZED MOLECULES FOR ELECTROCOALESCENT/MAGNETIC SEPARATION (ECMS) REMOVAL OF CONTAMINANTS FROM WATER STREAMS

[75] Inventor: Dennis E. J. Johnson, Aurora, Ill.

[73] Assignee: Aqua-Ion Systems, Inc., Littleton, Colo.

[21] Appl. No.: 377,621

[22] Filed: Jan. 25, 1995

[51] Int. Cl.⁶ .................................................. C02F 1/32
[52] U.S. Cl. .......................... 210/192; 210/205; 210/223; 422/186.12; 422/186.18; 422/186.3
[58] Field of Search ............................ 210/748, 695, 210/192, 198.1, 205, 222, 223; 422/24, 186.12, 186.18, 186.3

[56] References Cited

U.S. PATENT DOCUMENTS

| | | | |
|---|---|---|---|
| 3,186,929 | 6/1965 | Rippie | 204/155 |
| 3,697,420 | 10/1972 | Blaisdell et al. | 210/695 |
| 4,094,783 | 6/1978 | Jackson | 210/703 |
| 4,141,830 | 2/1979 | Last | 210/192 |
| 4,156,652 | 5/1979 | Wiest | 422/186.3 |
| 4,179,616 | 12/1979 | Coviello et al. | 422/186.3 |
| 4,238,326 | 12/1980 | Wolf | 210/695 |
| 4,343,707 | 8/1982 | Lucas | 210/695 |
| 4,382,866 | 5/1983 | Johnson | 210/748 |
| 4,562,014 | 12/1985 | Johnson | 261/76 |
| 4,563,286 | 1/1986 | Johnson et al. | 210/721 |
| 4,640,782 | 2/1987 | Burleson | 210/748 |
| 4,655,933 | 4/1987 | Johnson et al. | 210/748 |
| 4,857,204 | 8/1989 | Joklik | 210/695 |
| 4,956,080 | 9/1990 | Josefik | 210/109 |
| 5,192,423 | 3/1993 | Duczmal et al. | 209/164 |
| 5,266,215 | 11/1993 | Engelhard | 210/764 |
| 5,439,595 | 8/1995 | Downey | 210/748 |
| 5,443,719 | 8/1995 | Johnson et al. | 210/101 |

FOREIGN PATENT DOCUMENTS 478770 7/1929 Germany .
WO8102685 10/1981 WIPO .

*Primary Examiner*—Peter A. Hruskoci
*Attorney, Agent, or Firm*—Michael de Angeli

[57] ABSTRACT

An improved sterilizer for destroying biological contaminants in water comprises an annular water jacket through which the water stream flows, disposed around a high-intensity ultraviolet source comprising a number of lamps and a source of an intense magnetic field. Additionally, an air stream flows past the lamps, cooling the lamps, while being exposed to the ultraviolet radiation and the magnetic field, so that oxygen and nitrogen molecules in the atmospheric air stream are ionized. This ionized air stream is further mixed with the water stream to continually reduce and oxidize contaminants therein, and to promote coagulation of contaminants for physical filtration and removal.

17 Claims, 2 Drawing Sheets

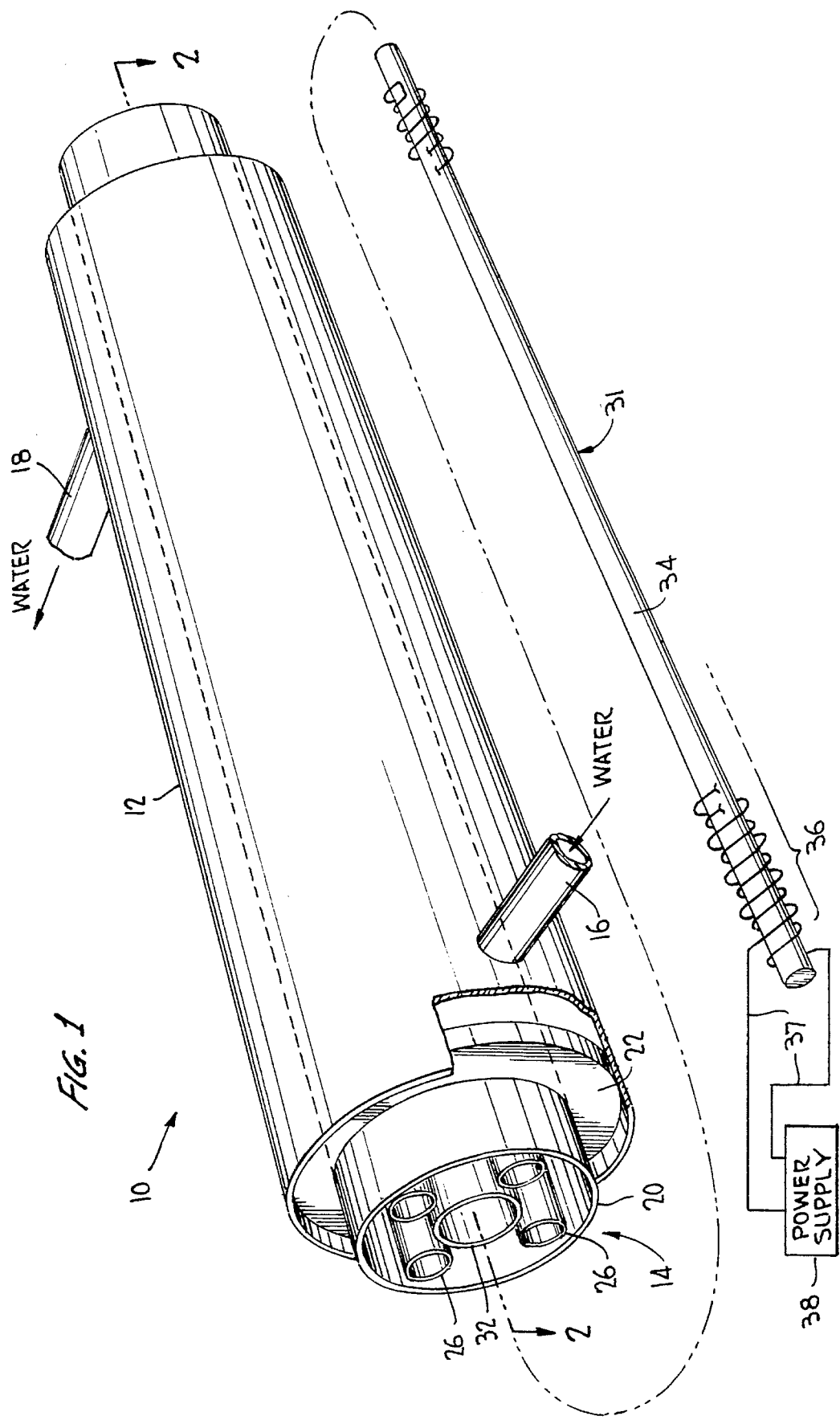

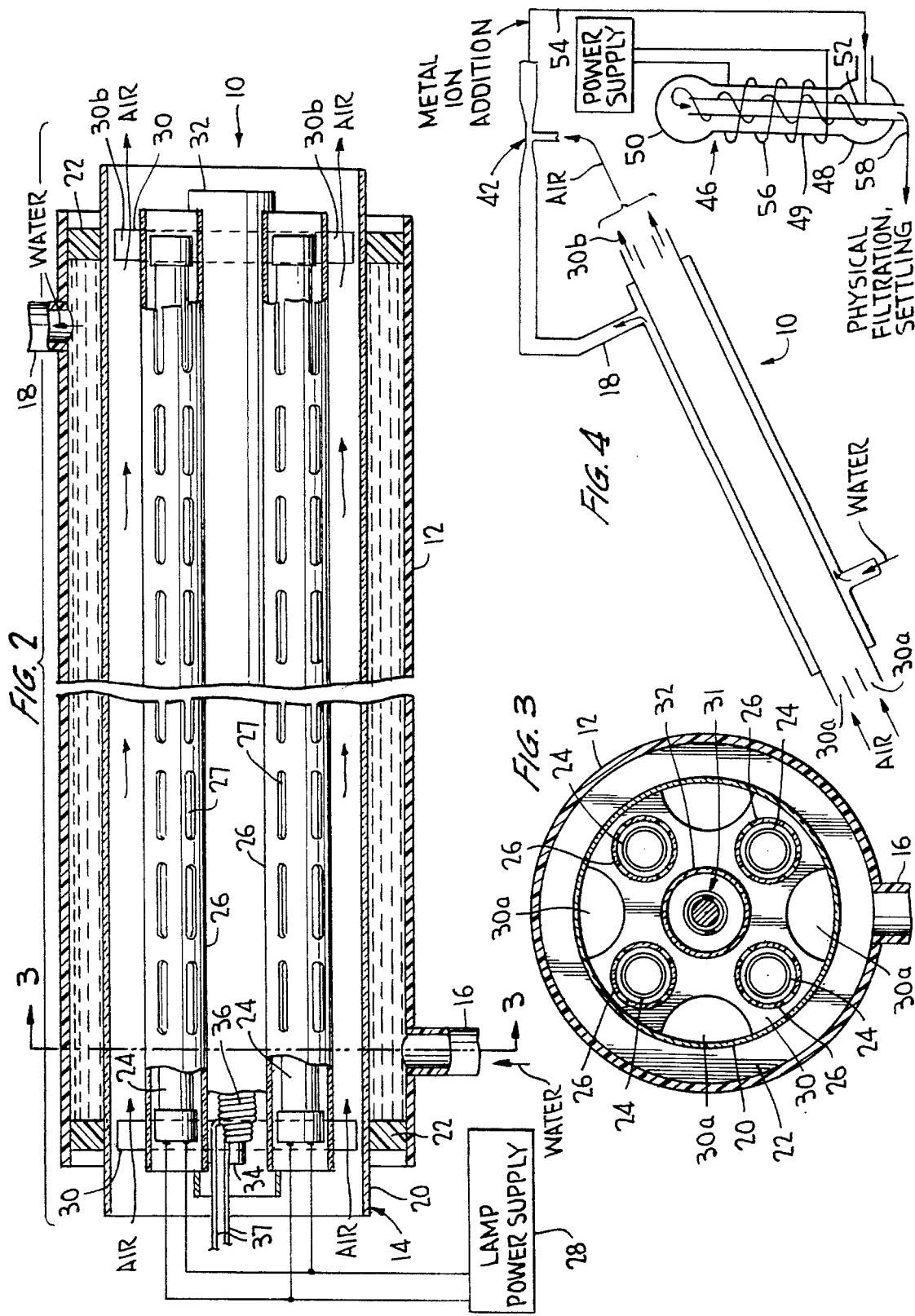

ULTRAVIOLET STERILIZER AND SOURCE OF IONIZED MOLECULES FOR ELECTROCOALESCENT/MAGNETIC SEPARATION (ECMS) REMOVAL OF CONTAMINANTS FROM WATER STREAMS

FIELD OF THE INVENTION

This invention relates to an improved short wavelength ultraviolet sterilizer for sterilizing biologically contaminated water streams. The sterilizer can be additionally configured to provide a stream of air including a substantial fraction of ionized gas molecules, for use in an electro-coalescent/magnetic separation (ECMS) system removing colloidal and solid contaminants from a water stream.

BACKGROUND OF THE INVENTION

The present inventor has been working for many years in the field of removal of contaminants from water streams without addition of chlorine or other disinfecting or coagulating chemicals thereto. Without implying any limitation on the scope of the invention disclosed and claimed herein, the inventor's efforts have been largely directed to removal of dissolved and ionized compounds and contaminants by exposing the water stream to one or more of ionized gas molecules, strong electric or magnetic fields, and metal ions, all of which tend, under appropriate circumstances, to "coagulate" or "agglomerate" the contaminants into larger particles, which can then be removed from the water stream by physical or electrically and/or magnetically stimulated filtration processes. This process is referred to as electrocoalescent/magnetic separation (ECMS).

More specifically, the inventor, in some cases with other inventors, has been granted U.S. Pat. Nos. 4,382,866, 4,562,286, 4,655,933, and 4,562,014, all directed generally to this subject matter, and disclosing various specific devices useful in ECMS water treatment systems. More recently, the inventor and another filed copending application Ser. No. 08/200,749 on Feb. 23, 1994, and the inventor filed Ser. No. 08/326,339 on Oct. 20, 1994.

Ser. No. 08/200,749, which is incorporated herein by this reference, is directed, as indicated generally above, to removal of contaminants from a water stream by adding ionized gases and other materials to a water stream and subjecting the water stream to a combination of electric and magnetic fields under specific flow conditions.

Ser. No. 08/326,339, also incorporated herein by reference, is again directed to removal of contaminants from water streams by mixing ionized materials with the water stream and subjecting the stream to electric and magnetic fields where appropriate. This application discloses an apparatus for exposing a stream of atmospheric air to ultraviolet light in the presence of electric and/or magnetic fields, such that a substantial fraction of the molecules of the air are ionized, forming ionized oxygen, including singlet molecular oxygen, ozone, and ionized nitrogen molecules. The ionized molecules promote oxidation and reduction of contaminants, and promote coagulation thereof for subsequent physical filtration. Ser. No. 08/326,339 also shows a convenient device for introducing metal ions into the water stream, further promoting coagulation of contaminants for subsequent physical removal by filtration, and forming bactericidal, viricidal, and fungicidal compounds in situ, so as to efficiently remove biological contaminants from the water stream. The inventor has also pending application Ser. No. 08/377,620, filed concurrently herewith (Attorney's Docket No. DJ-3), and incorporated by reference herein, directed to ECMS systems for removal of contaminants from water, including desalinization, and disclosing further preferred components and methods for non-chemical removal of contaminants from streams of water.

The prior art is well aware of the utility of ultraviolet and other electromagnetic radiation in disinfecting water, primarily by destroying organic molecules, including bacteria, viruses, and fungi, upon exposure to high-intensity short wavelength ultraviolet light. There are numerous references showing the utility of such processes. It would be desirable to make more efficient use of the radiation from a particular source than is now done, and in particular to combine the biocidal effect of ultraviolet radiation with the utility of simultaneous exposure of the water stream to a magnetic field. Still further, it would be desirable to simultaneously expose a stream of atmospheric air to ultraviolet radiation and a magnetic field in order to generate ions from the atmosphere for promoting oxidation, reduction, and coagulation, and for destruction and removal of contaminants in a water stream.

OBJECTS OF THE INVENTION

It is therefore an object of the invention to provide an ultraviolet sterilizer of improved efficiency.

It is a further object of the invention to provide an ultraviolet sterilizer of improved efficiency integrated with means for exposing the ultraviolet lamps and water stream to a magnetic field.

It is a further object of the invention to provide an ultraviolet sterilizer, defining a flow path for water to be exposed to biocidal ultraviolet radiation, and further defining an air flow path whereby atmospheric air is simultaneously exposed to ultraviolet radiation from the same source, such that a substantial fraction of molecules in the air are ionized, and combined with means for mixing the streams of air and water.

It is a further object of the invention to provide an ultraviolet sterilizer wherein a water stream is exposed to ultraviolet radiation as well as a magnetic field, and wherein a stream of air is simultaneously exposed to ultraviolet radiation and a magnetic field from the same sources, combined with means for mixing the ionized air and contaminated water streams together.

It is a further object of the invention to provide designs for the sterilizer and associated equipment mentioned above such that these components can be fabricated and assembled to the greatest possible degree using readily-available components and materials, in particular so that the benefits of the invention are available in countries not having a substantial manufacturing base.

SUMMARY OF THE INVENTION

These and other objects and aspects of the invention and needs of the art are satisfied by the present invention, whereby an improved sterilizer, for use in ECMS systems and elsewhere, comprises a water jacket defining an inlet and outlet for water, disposed about a central source of radiation, including both ultraviolet radiation and a magnetic field. The source of the magnetic field may comprise a steel rod wrapped by a coil at the center of a number of ultraviolet lamps spaced around the rod and extending parallel thereto. The lamps may be disposed within a cylindrical quartz glass window, sealed at either end to the water jacket. The lamps and the coil providing the magnetic field may be supported within the cylindrical glass window by spacers defining an air inlet and outlet, whereby an air flow path is established, such that the air and water streams are separated but are simultaneously exposed to the ultraviolet radiation and to the magnetic field. Biological contaminants, including bacteria, fungi, and viruses, in the water are destroyed by exposure to very intense short wavelength ultraviolet radiation, while the presence of the magnetic field serves to assist coagulation and promote oxidation and reduction of contaminants in the water. The air stream, including a substantial fraction of ionized oxygen and nitrogen gas molecules produced upon exposure to the ultraviolet radiation and magnetic field, is subsequently mixed with the water stream. In the presence of dissolved ionized gas, the coagulant effect is thus significantly intensified, as are oxidation and reduction of contaminants in the water stream. The water stream can then be supplied to physical filtration units and the like for ECMS removal of contaminants from the water stream.

BRIEF DESCRIPTION OF THE DRAWINGS

The invention will be better understood if reference is made to the accompanying drawings, in which:

FIG. 1 shows a perspective view of the sterilizer according to the invention, having had the magnetic field source removed therefrom for clarity;

FIG. 2 shows a cross-section along the line 2—2 of FIG. 1;

FIG. 3 shows a cross-section along the line 3—3 of FIG. 2; and

FIG. 4 shows a schematic view of an exemplary ECMS system for purification of water according to the invention, incorporating the sterilizer of FIGS. 1–3.

DESCRIPTION OF THE PREFERRED EMBODIMENTS

FIGS. 1–3 show the sterilizer according to the invention. Water flows through a water jacket in which it is exposed to ultraviolet radiation and to a magnetic field; in the preferred embodiment, air flows within the interior of the water jacket, and is exposed to ultraviolet radiation and the magnetic field from the same sources. Sterilizer assembly 10 thus comprises a cylindrical water jacket 12 comprising an outer PVC or metal tube sealed at either end to a central assembly 14 comprising sources of ultraviolet radiation and of a magnetic field within a quartz glass reactor tube 20. Contaminated water enters water jacket 12 through an inlet 16 and exits through an outlet 18.

The central assembly 14, including a source of magnetic field and a source of ultraviolet radiation, is assembled within a cylindrical quartz glass reactor tube 20 supported within and sealed to the water jacket 12 by annular seal members 22. Cylindrical glass tube 20 thus forms a radiation-transparent window. Within window 20 are disposed a number (in the example shown, four) of conventional low-pressure mercury vapor disinfection ultraviolet lamps 24 supported within a like number of ultraviolet radiation-transparent quartz tubes 26. As indicated in FIGS. 2 and 3, quartz tubes 26 may be perforated at a number of locations 27 to allow air circulation around the lamps 24, preventing overheating in extended use. Lamps 24 are powered by a conventional lamp ballast AC power supply 28. Preferably lamps 24 emit a substantial proportion of ultraviolet radiation in the frequencies known to be destructive to biological contaminants, e.g., 254 and 185 nm ultraviolet radiation. Such lamps are commercially available, as are suitable power supplies. Provision of quartz tubes 26 as supports for lamps 24 allows the lamps 24 to be conveniently removed for replacement. Typically, tubes 26 are supported by spacer members 30 fitting snugly within glass tube 20.

A central radiation transparent tube 32, typically also formed of quartz, is also supported by the spacer members 30. Magnetic field source 31 disposed within tube 32 comprises a solid steel rod 34 surrounded by a coil 36 of wire connected to a DC power supply 38. Preferably, as shown in FIG. 1, the coil 36 of wire is wrapped helically about rod 34, extending from one end of the rod to the opposite end, and back so as to provide a double-layer coil, and also so that the leads 37 extend out one end of the sterilizer assembly 14.

When power supply 38 is energized, source 31 emits a solenoidal magnetic field, extending throughout the interior of water jacket 12 and promoting oxidation and reduction of contaminants in water therein, polarizing contaminant molecules, and promoting coagulation thereof. Dust within the tube 30 will also be attracted to the surface of tube 32 by the magnetic field emitted by source 31, away from the surfaces of tubes 26, such that dust thereon does not interfere with ultraviolet transmission therethrough. The inventor also considers that subjecting water to be treated to ultraviolet radiation and a magnetic field simultaneously increases the biocidal efficiency of the ultraviolet radiation, but the invention is not constrained by this theory.

As indicated above, it is an object of the invention to provide designs for apparatus providing the benefits of the invention using commonly-available materials and components. To this end, magnetic field source 31 may comprise a core 34 of 5/16 inch mild steel rod wrapped by at least two layers of #18 insulated wire. The end spacer members 30 may be machined of Teflon or another UV-resistant plastic material, while the annular seal members 22 may be machined of PVC plastic. The outside diameter of the quartz glass reactor tube 20 and the inside diameter of water jacket 12 bear the approximate ratio of 1:1.75. Water jacket 12, together with inlet and outlet tubes 16 and 18 may be formed of PVC plastic or of metal. Tubes 20, 26 and 32 may all be formed of quartz glass, which is substantially transparent to both ultraviolet radiation and the magnetic field emitted by the source 31.

As indicated in FIG. 3, the spacer members 30 are provided with cutout air passages as shown at 30a, spaced evenly between tubes 26 receiving lamps 24, for passage of air therethrough. Air passage therethrough is important in cooling the lamps, as indicated above. However, it will be appreciated by those of skill in the art that exposure of atmospheric air to ultraviolet radiation from lamps 24 as well as the magnetic field emitted by the coil 31 will result in some substantial fraction of the molecules of the air being ionized, forming ionized oxygen, including singlet molecular oxygen, ozone, and nitrogen molecules. According to one aspect of the invention, such ionized molecules oxidize and reduce contaminants in a water stream and also coagulate the contaminants for subsequent electrically and magnetically stimulated filtration. The overall process of electrically coalescing contaminants and magnetically separating the contaminants from the water stream is referred to as electro-coalescent/magnetic separation (ECMS).

For convenient use of the sterilizer in an ECMS system, according to a further aspect of the invention, an air flow path is defined through central assembly 14, extending from inlet openings 30a in one end of the sterilizer assembly 10, and exiting corresponding outlet openings 30b at the opposite end thereof. Preferably, the sterilizer 10 is inclined with respect to the horizontal, as shown in FIG. 4, such that the air inlet is at the lower end and the air outlet is at the upper end, so that convection assists in drawing the airstream through the sterilizer assembly 10. A small low pressure blower could also be employed. The air stream having been exposed to ultraviolet radiation and the magnetic field is then mixed with the water stream exiting the sterilizer assembly 10. Preferably, the water stream is constrained to flow through a venturi 42, and the air stream is introduced at a low pressure point thereof, such that the air stream is drawn into the contaminated water stream and mixed thoroughly therewith without the necessity of pumps or the like.

The mixed water and air streams may then be introduced into a further mixing chamber device 46, e.g., as disclosed in Ser. No. 08/200,749, incorporated herein by reference, for further mixing. As indicated schematically, mixing device 46 comprises a lower mixing chamber 48, connected to an intermediate tubular section 49, and thence to an upper chamber 50. Water enters the lower chamber 48 off-axis, and flows upwardly in a spiral pattern, around an exit tube 52. The effect is to provide very thorough mixing of the air and water streams, together with any metal ions that may be added at 54 (e.g., employing equipment also shown in Ser. No. 08/200,749). A magnetic field may also be applied, as indicated at 56. The coagulated contaminants are then physically filtered from the stream as indicated at 58. The overall contaminant removal process is termed ECMS, as indicated, and in this case further incorporating UV sterilization. The filtration step may be performed using components disclosed in Ser. No. 08/377,620, filed concurrently herewith (Attorney's Docket No. DJ-3).

Thus, it can be seen that there has been described a sterilizer unit meeting the objects of the invention. The configuration of the sterilizer of the invention provides very efficient use of the ultraviolet energy emitted by the lamps in that all energy emitted by from the lamps 24 passes through the water at least once. If desired, the inner surface of the water jacket 12 may be provided with a reflective layer of metal, such as aluminum, stainless steel, or the like, to reflect back any ultraviolet energy not absorbed into the water stream. Passing the ultraviolet energy through air flowing through the sterilizer, and then mixing the air having been irradiated with the water stream, provides a two-fold improvement. Firstly, if the air were simply used for cooling lamps 24 and then released to the atmosphere, absorption of the ultraviolet radiation by oxygen molecules in the air would reduce the efficiency of the ultraviolet irradiation of the water stream without advantage being taken. Further, by mixing a stream of air, containing a substantial fraction of ionized oxygen and nitrogen molecules, with the water stream, reduction and oxidation of contaminants in the water are further promoted, as is coagulation of the contaminants for physical removal from the water stream.

The method according to the invention thus includes the steps of admitting a stream of water to a sterilizer including sources of ultraviolet radiation and a magnetic field, the sterilizer defining a water flow path and an air flow path, such that streams of air and of water are simultaneously exposed to the ultraviolet radiation and the magnetic field, thus destroying biological contaminants, including bacteria, viruses, fungi, as well as mixing the streams of water and air, and removing coagulated particulates, having been oxidized and reduced, and fragments of biological contaminants, and the like, from the water stream.

While a preferred embodiment of the invention has been disclosed, it will be appreciated by those of skill in the art that numerous modifications can be made thereto without departure from the spirit and scope of the invention. Moreover, it will be appreciated that the sterilizer of the invention can be incorporated in many different types of systems for purifying and processing streams of water, the precise components thereof depending on the constituents of the water to be treated. Therefore, the invention should not be limited by the above disclosure, which is exemplary only, but only by the following claims.

What is claimed is:

1. An improved radiation sterilizer for destroying microorganisms in a stream of water, comprising:

a source of electromagnetic radiation, disposed centrally within an elongated water jacket, said water jacket having a water inlet at a first end thereof and a water outlet at a second end thereof, said source being sealed from water flowing in said water jacket by a cylindrical radiation-transparent glass window, such that water flowing within said water jacket from said inlet to said outlet is exposed to radiation from said source, said source of electromagnetic radiation comprising an elongated central magnetic field source surrounded by a plurality of elongated ultraviolet lamps, and power supplies for energizing said lamps and said magnetic field source, wherein said lamps extend parallel to and are spaced around said magnetic field source, such that said lamps and water within said water jacket are exposed to the magnetic field from said source.

2. The sterilizer of claim 1, wherein said central magnetic field source comprises a ferromagnetic rod surrounded by a coil of insulated wire.

3. The sterilizer of claim 2, wherein said ferromagnetic rod is solid steel.

4. The sterilizer of claim 2, wherein said coil of wire comprises at least two complete wraps of wire extending along said rod for a distance corresponding substantially to the length of said lamps.

5. The sterilizer of claim 1, wherein said lamps are each disposed in ultraviolet-transparent tubes, said tubes extending parallel to one another and being supported by spacer means at either end of said cylindrical glass window.

6. The sterilizer of claim 5, wherein said ultraviolet-transparent tubes are formed of quartz glass.

7. The sterilizer of claim 5, wherein said ultraviolet-transparent tubes are perforated at a plurality of locations, to allow ambient air to circulate therethrough, to prevent overheating of said lamps.

8. The sterilizer of claim 5, wherein said spacer means at either end of said cylindrical glass window are provided with air passages, to encourage convective flow of air through the interior of said cylindrical glass window, to prevent overheating of said lamps.

9. The sterilizer of claim 1, wherein said elongated central magnetic field source is supported within a glass tube disposed substantially at the center of said cylindrical glass window.

10. The sterilizer of claim 1, wherein said lamps and said elongated central magnetic field source are supported within said cylindrical glass window by spacer means defining an air inlet at one end of said sterilizer and an air outlet at an opposed end of said sterilizer, such that a stream of ambient air flows through said sterilizer and is exposed to ultraviolet radiation and a magnetic field therein.

11. In combination, the sterilizer of claim 10, and means for mixing the stream of air, having been exposed in said sterilizer to ultraviolet radiation and a magnetic field, with the stream of water from the outlet of said sterilizer.

12. The combination of claim 11, wherein said means for mixing the stream of air with the stream of water comprises a venturi through which said stream of water flows, and means for introducing said stream of air at a reduced-pressure point therein.

13. The combination of claim 11, in further combination with means for separating contaminants in said water stream, having been coagulated upon passage through said sterilizer and mixture with said stream of air, from said water stream.

14. Apparatus for treating a contaminated stream of water, comprising:

a sterilizer comprising sources of ultraviolet radiation and of a magnetic field, said sterilizer defining a water flow path, such that said stream of contaminated water flows past said sources of ultraviolet radiation and of a magnetic field, such that said stream of water is exposed thereto, and said sterilizer further defining an air flow path, such that a stream of ambient air flows past said sources of ultraviolet radiation and of a magnetic field, and is exposed thereto;

means for mixing said streams of water and air, having been simultaneously exposed to said sources of ultraviolet radiation and a magnetic field, with one another, in order that contaminants in said water stream are disinfected, oxidized, reduced, polarized, and/or coagulated with one another; and means for separating said contaminants from said water stream;

wherein said sterilizer comprises an elongated central magnetic field source surrounded by a plurality of elongated ultraviolet lamps, said magnetic field source and said lamps being connected to power supplies for energizing said lamps and said magnetic field source, and wherein said lamps extend parallel to and are spaced around said magnetic field source.

15. The apparatus of claim 14, wherein said ultraviolet lamps and said source of a magnetic field are both disposed centrally within an elongated water jacket, said water jacket having a water inlet at a first end thereof and a water outlet at a second end thereof, said ultraviolet lamps and magnetic field source being sealed from water flowing in said water jacket by a cylindrical radiation-transparent glass window, such that contaminated water flowing within said water jacket from said inlet to said outlet is exposed to ultraviolet radiation and said magnetic field, and wherein said air flow path further extends through said cylindrical radiation-transparent glass window, whereby said streams of ambient air and of water are substantially simultaneously exposed to ultraviolet radiation and a magnetic field from said sources thereof.

16. The apparatus of claim 14, wherein said means for mixing said streams of water and air comprises a venturi through which said stream of water flows, and means for introducing said stream of air thereto at a reduced-pressure point thereof.

17. The apparatus of claim 14, wherein said lamps and said elongated central magnetic field source are supported within said cylindrical glass window by spacer means defining an air inlet at one end of said sterilizer and an air outlet at an opposed end of said sterilizer, defining said air flow path along which said stream of air flows through said sterilizer to be exposed to ultraviolet radiation and a magnetic field therein.

* * * * *